(12) United States Patent
Yoo

(10) Patent No.: US 9,436,350 B2
(45) Date of Patent: Sep. 6, 2016

(54) METHOD OF REALIZING USER MENU EDIT FUNCTION

(75) Inventor: Bong Soo Yoo, Seoul (KR)

(73) Assignee: SAMSUNG MEDISON CO., LTD., Hongcheon-Gun, Gangwon-Do (KR)

( * ) Notice: Subject to any disclaimer, the term of this patent is extended or adjusted under 35 U.S.C. 154(b) by 222 days.

(21) Appl. No.: 13/992,691

(22) PCT Filed: May 13, 2011

(86) PCT No.: PCT/KR2011/003565
§ 371 (c)(1),
(2), (4) Date: Sep. 18, 2013

(87) PCT Pub. No.: WO2012/077876
PCT Pub. Date: Jun. 14, 2012

(65) Prior Publication Data
US 2014/0109006 A1    Apr. 17, 2014

(30) Foreign Application Priority Data

Dec. 7, 2010    (KR) .......................... 10-2010-0124012

(51) Int. Cl.
G06F 3/0482    (2013.01)
A61B 8/00    (2006.01)
G06F 19/00    (2011.01)

(52) U.S. Cl.
CPC .............. G06F 3/0482 (2013.01); A61B 8/465 (2013.01); G06F 19/3406 (2013.01)

(58) Field of Classification Search
CPC ..................................................... G06F 3/0482
USPC ........................................................ 715/810
See application file for complete search history.

(56) References Cited

U.S. PATENT DOCUMENTS

| 5,437,008 A * | 7/1995 | Gay et al. .................. 715/205 |
| 7,022,075 B2 | 4/2006 | Grunwald et al. |
| 2007/0265935 A1* | 11/2007 | Woycik ................ G06Q 20/367 705/65 |
| 2010/0262936 A1* | 10/2010 | Shimizu et al. ............. 715/810 |

FOREIGN PATENT DOCUMENTS

| JP | 08-044851 A | 2/1996 |
| KR | 10-2004-0066836 A | 7/2004 |
| KR | 10-2010-0011669 A | 2/2010 |
| KR | 10-2011-0051375 A | 5/2011 |

OTHER PUBLICATIONS

Korean Notice of Allowance dated Jan. 14, 2013 issued in Korean Patent Application No. 10-2010-0124012 (English translation).
International Search Report dated Dec. 20, 2011 issued in International Patent Application No. PCT/KR2011/003565 (English translation).

* cited by examiner

Primary Examiner — Andrea Leggett
(74) Attorney, Agent, or Firm — McDermott Will & Emery LLP

(57) ABSTRACT

Disclosed is a method of realizing a user menu edit function, including (a) providing a list of menu items selectable on a per mode basis, (b) receiving selection of at least one from the list of menu items input by a user, (c) applying the menu item selected by the user to a diagnostic screen application field linked to a real screen of a diagnostic apparatus, and (d) displaying the menu item selected by the user on the real screen of the diagnostic apparatus in response to the application result.

10 Claims, 3 Drawing Sheets

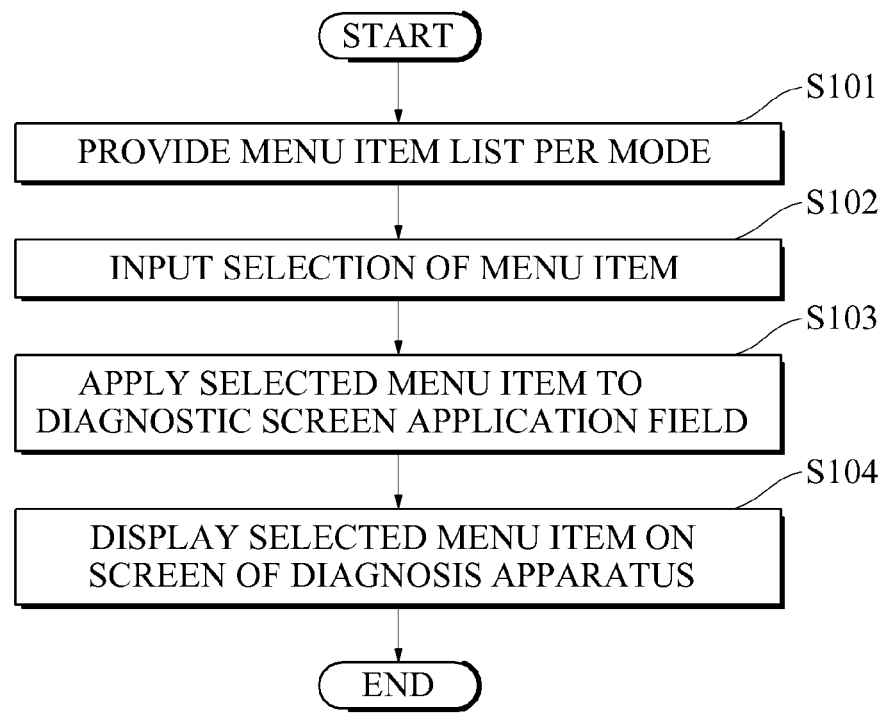

METHOD OF REALIZING USER MENU EDIT FUNCTION

RELATED APPLICATIONS

This application is the U.S. National Phase under 35 U.S.C.§371 of International Application No. PCT/KR2011/003565, filed on May 13, 2011, which in turn claims the benefit of Korean Application No. 10-2010-0124012, filed on Dec. 7, 2010, the disclosures of which Applications are incorporated by reference herein.

TECHNICAL FIELD

Embodiments of the present invention relate to a method of realizing a user menu edit function, which allows a user to conveniently edit menu items with regard to each operation mode preferred or mainly used by the user in a variety of diagnostic apparatuses, such as an ultrasound diagnostic apparatus and the like.

BACKGROUND ART

Generally, a variety of diagnostic apparatuses, such as an ultrasound diagnostic apparatus and the like, are becoming more complex and including a more diverse array of functions, and thus menu items, which are displayed on the diagnostic apparatus, are diversifying and the number of menu items is increasing. In this case, menu items of each diagnostic apparatus are not arranged according to a user action pattern, but are arranged according to a formulary pattern that is uniformly set by product developers at the launch of products, which results in inconvenience when the user selects desired menu items.

In particular, in the case of diagnostic apparatuses that are complex, include a diverse array of functions and require special knowledge to operate, the aforementioned problems are becoming more serious issues.

In addition, conventional medical diagnostic apparatuses are configured in such a way that some menu items which are frequently used menu items and some menu items which are not are used often are displayed together on a per stage basis without distinction. This results in very complicated arrangement of the displayed menu items, causing the user difficulty in searching for and selecting desired menu items.

DISCLOSURE

Technical Problem

It is an aspect of the present invention to provide a method of realizing a user menu edit function, which allows a user to conveniently edit menu items with regard to each operation mode preferred or mainly used by the user in a variety of diagnostic apparatuses, such as an ultrasound diagnostic apparatus and the like.

Technical Solution

In accordance with one aspect of the present invention, a method of realizing a user menu edit function, includes (a) providing a list of menu items selectable on a per mode basis, (b) receiving selection of at least one from the list of menu items input by a user, (c) applying the menu item selected by the user to a diagnostic screen application field linked to a real screen of a diagnostic apparatus, and (d) displaying the menu item selected by the user on the real screen of the diagnostic apparatus in response to the application result.

An attribute edit field to edit at least one attribute with regard to the menu item selected in operation (b) may be further provided.

Attributes that the user may edit in the attribute edit field may include names and importance factors of the respective menu items as well as names of classified groups.

An auto-alignment field to determine alignment criteria of the menu items on the real screen of the diagnostic apparatus may be further provided, and the auto-alignment field may allow the menu items to be aligned based on attributes of the respective menu items, which originally stored or edited in the attribute edit field.

The respective menu items may be set so as to be displayed on a per page basis on the real screen of the diagnostic apparatus using the diagnostic screen application field.

The menu item selected in operation (c) may be applied to the diagnostic screen application field as the user drags and drops the selected menu item in the diagnostic screen application field, or may be applied to the diagnostic screen application field via selection of the menu item and via selection of a specific position in a desired page on the diagnostic screen application field.

The menu items may be aligned and provided in alphabetical order or on a per attribute basis.

In operation (a) of providing the list of the menu items, a grouping field for grouping of a plurality of menu items from the list of the menu items may be further provided.

A group of the menu items that the user groups using the grouping field may be displayed in the real screen of the diagnosis apparatus.

An application coverage edit field to edit the setting range of a diagnosis application with regard to the menu item selected in operation (b) may be further provided, or an application coverage edit field to determine the setting range of a diagnosis application to be applied on a per page basis in the diagnostic screen application field may be further provided.

Advantageous Effects

According to the embodiment of the present invention, when using variety of diagnostic apparatuses, such as an ultrasound diagnostic apparatus and the like, the user may conveniently edit menu items with regard to each operation mode preferred or mainly used by the user.

DESCRIPTION OF DRAWINGS

FIG. 3 is a flowchart explaining a method of realizing a user menu edit function according to the embodiment.

BEST MODE

Hereinafter, the embodiments of the present invention will be described in more detail. These embodiments are provided by way of example of the present invention, and the scope of the disclosure is not limited to these embodiments.

Figure 1:
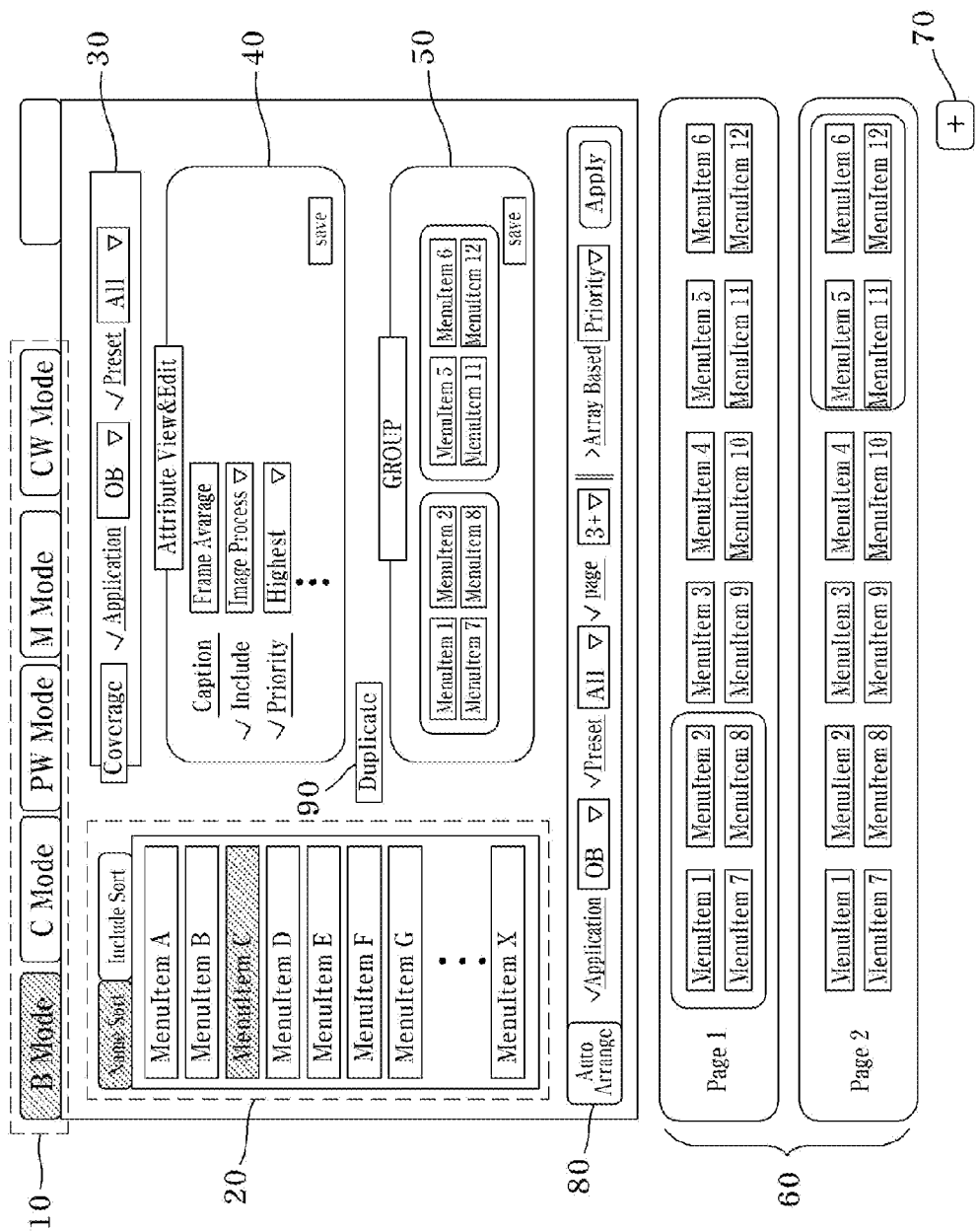
FIG. 1 is a view showing a user menu edit screen provided by a method of realizing a user menu edit function according to one embodiment of the present invention.
Figure 2:
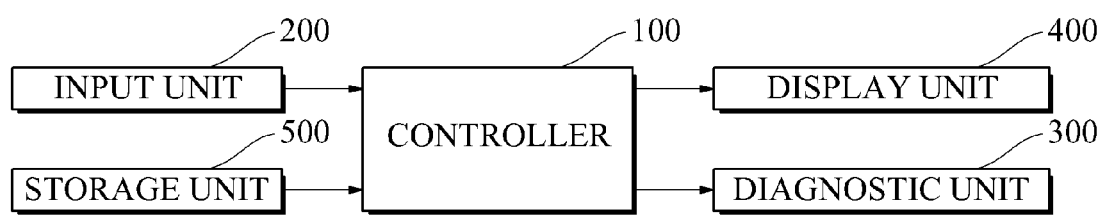
FIG. 2 is a schematic view showing a system configuration according to the embodiment.

FIG. 1 is a view showing a user menu edit screen provided by a method of realizing a user menu edit function according to one embodiment of the present invention, FIG. 2 is a schematic view showing a system configuration according to the embodiment, and FIG. 3 is a flowchart explaining a method of realizing a user menu edit function according to the embodiment.

The method according to the embodiment, as exemplarily shown in FIG. 2, is applicable to a variety of diagnostic apparatuses. Each diagnostic apparatus includes a controller 100 to control the entire system, an input unit 200 to receive various user selections or inputs, a diagnostic unit 300 for various diagnoses of a subject, a display unit 400 to display a variety of menu items or images indicating diagnosed results, and a storage unit 500 in which various user input data, menu setting data as well as data regarding diagnosed results are stored. The method of realizing a user menu edit function according to the present embodiment is mainly realized by interaction between the controller 100, the input unit 200, the display unit 400, and the storage unit 500.

The method of realizing a user menu edit function according to the present embodiment will be described as follows with reference to FIGS. 1 to 3.

First, the controller 100 controls provision of a list of menu items selectable on a per mode basis (S101). More specifically, as exemplarily shown in FIG. 1, tabs on a per mode basis are provided in a region 10, and a list of menu items selectable on a per selected mode basis is provided in a region 20. For example, in the case of an ultrasound diagnostic apparatus, the region 10 is provided with tabs with regard to ultrasound image modes of the ultrasound diagnostic apparatus including, e.g., a Brightness (B) mode, a Color (C) mode, a Pulsed-Wave (PW) mode, a Motion (M) mode, and a Continuous Wave (CW) mode. In addition, for example, if the B mode is selected, the region 20 is provided with a list of selectable menu items based on the B mode including, e.g., 'Focus', 'Frame average', 'Power', and 'Rotation' items. In this case, the menu items provided in the region 20 may be aligned and provided in alphabetical order or on a per attribute basis based on selection of a name sort tab, an attribute sort tab, or the like as exemplarily shown.

Next, selection of at least one menu item from the list of menu items is input by the user via the input unit 200 (S102). More specifically, selection of a menu item to be edited and displayed on a real screen of the diagnostic apparatus is input via the input unit 200.

Then, the controller 100 applies the menu item, selected by the user, to a diagnostic screen application field 60 that is linked to the real screen of the diagnostic apparatus (S103). More specifically, if at least one menu item is selected by the user in operation S102, the menu item is applied to the diagnostic screen application field 60 linked to the real screen of the diagnostic apparatus, such that the selected menu item is activated in a specific page of the diagnostic screen application field 60. Here, "linkage with the real screen" means that content applied to the diagnostic screen application field 60 is displayed on the real screen of the diagnostic apparatus. In this case, the diagnostic screen application field 60 may be set such that each menu item is displayed on a per page basis (page 1, page 2, . . . ) on the real screen of the diagnostic apparatus, and the number of pages may be increased using a button of a region 70. In addition, in operation S103, the user may drag and drop the selected menu item in the diagnostic screen application field 60, and may apply the selected menu item to the diagnostic screen application field 60 by selecting the menu item and by selecting a specific position in a desired page on the diagnostic screen application field 60 (for example, the user may select 'Gain' from the menu item list, and thereafter select 'MenuItem 8' in page 2 the diagnostic screen application field 60).

Next, the controller 100 controls display of the at least one menu item selected by the user on the real screen of the diagnostic apparatus in response to the application result of operation S103 (S 104). Thereby, the at least one menu item applied on a per page basis in the diagnostic screen application field 60 in operation S103 may be displayed on the real screen of the diagnostic apparatus so as to be selected by the user. Through the aforementioned operations, when the user uses various diagnostic apparatuses including the ultrasound diagnostic apparatus and the like, it may be possible to allow the user to conveniently and freely select menu items with regard to each operation mode that the user prefers or mainly uses.

Meanwhile, in the present embodiment, if a specific menu item is selected in operation S102, an attribute edit field 40 to edit at least one attribute with regard to the menu item may be further provided. Examples of attributes provided in the attribute edit field 40 that the user can edit may include names and importance factors of the respective menu items as well as classified group names for classification and grouping of the items on a per attribute basis.

In addition, in the present embodiment, when providing the menu item list in operation S101, a grouping field 50 for selection and grouping of a plurality of menu items from the menu item list may be further provided. The grouping field 50 serves to assist the user in grouping and simultaneously using some menu items selected from among a plurality of menu items. As such, a group of the menu items that the user groups using the grouping field 50 is displayed on the real screen of the diagnostic apparatus.

In addition, in the present embodiment, if a specific menu item is selected in operation S102, an application coverage edit field 30 to edit the setting range of a diagnosis application (for example, a diagnosis department) with regard to the selected menu item may be further provided. Through provision of the application coverage edit field, the user may set a menu item to be displayed on the screen on a per diagnosis application basis or on a per diagnosis department basis.

According to embodiments, the application coverage edit field 30 may be configured to determine the setting range of the diagnosis application to be applied on a per page basis in the diagnostic screen application field 60.

In the present embodiment, additionally, an auto-alignment field 80 to determine alignment criteria of menu items on the real screen of the diagnostic apparatus is provided. The auto-alignment field 80 allows the menu items to be aligned based on attributes of the respective menu items, which originally stored or edited in the attribute edit field 40. Thereby, the user may preset the alignment criteria of the menu items on the real screen of the diagnostic apparatus, which assists the user in more conveniently performing diagnosis.

In the present embodiment, additionally, an iterative setting field 90 to iteratively set a plurality of menu items whenever a menu item button is pushed is provided. In this case, it may be necessary to preset requirements for activation of the iteratively set menu items so as not to conflict with one another.

As described above, according to the present embodiment, when using variety of diagnostic apparatuses, such as an ultrasound diagnostic apparatus and the like, the user may conveniently edit menu items with regard to each operation mode preferred or mainly used by the user.

The invention claimed is:

1. A method of realizing a user menu edit function in an ultrasound diagnostic apparatus, the method comprising:
   (a) providing a list of menu items selectable according to each of a plurality of ultrasound image modes, wherein the plurality of ultrasound image modes includes at least one of a Brightness (B) mode, a Color (C) mode, a Pulse-Wave (PW) mode, a Motion (M) mode and a Continuous Wave (CW) mode, wherein the list of menu items includes at least one of a Focus item, a Frame average item, a Power item and a Rotation item;
   (b) receiving selection of at least one from the list of menu items input by a user;
   (c) applying the menu item selected by the user to a specific position in a plurality of pages of a diagnostic screen application field linked to a real screen of the ultrasound diagnostic apparatus; and
   (d) displaying the menu item selected by the user on the real screen of the ultrasound diagnostic apparatus in response to the application result,
   wherein the plurality of pages are displayed in different areas of the diagnostic screen application field based on a diagnostic application, and
   wherein the operation (d) comprises displaying an application coverage edit field to edit a setting range of a diagnosis department with regard to the selected menu item.

2. The method according to claim 1, wherein an attribute edit field to edit at least one attribute with regard to the menu item selected in the operation (b) is further provided.

3. The method according to claim 2, wherein attributes that the user may edit in the attribute edit field include names and importance factors of the respective menu items as well as names of classified groups.

4. The method according to claim 2, wherein an auto-alignment field to determine alignment criteria of the menu items on the real screen of the ultrasound diagnostic apparatus is further provided, and
   wherein the auto-alignment field allows the menu items to be aligned based on attributes of the respective menu items, which originally stored or edited in the attribute edit field.

5. The method according to claim 1, wherein the respective menu items are set so as to be displayed on a per page basis on the real screen of the ultrasound diagnostic apparatus using the diagnostic screen application field.

6. The method according to claim 1, wherein the menu item selected in the operation (c) is applied to the diagnostic screen application field as the user drags and drops the selected menu item in the diagnostic screen application field, or is applied to the diagnostic screen application field via selection of the menu item and via selection of the specific position in a desired page on the diagnostic screen application field.

7. The method according to claim 1, wherein the menu items are aligned and provided in alphabetical order or on a per attribute basis.

8. The method according to claim 1, wherein in the operation (a) of providing the list of the menu items, a grouping field for grouping of a plurality of menu items from the list of the menu items is further provided.

9. The method according to claim 8, wherein a group of the menu items that the user groups using the grouping field is displayed in the real screen of the ultrasound diagnosis apparatus.

10. The method according to claim 1, wherein the application coverage edit field determines the setting range of the diagnosis department to be applied on a per page basis in the diagnostic screen application field.

* * * * *